United States Patent [19]

Heinzelman et al.

[11] Patent Number: 5,695,481
[45] Date of Patent: Dec. 9, 1997

[54] NOZZLE

[75] Inventors: Bert D. Heinzelman, Tenafly, N.J.;
Theresa C. Desantis, Gibsonia, Pa.;
Susan M. Clement, Morris Plains, N.J.;
Robert W. Pritchard, Pittsburgh, Pa.;
Joseph A. Matthias, Andover, N.J.;
Jeffrey A. Karg, Ashland, Mass.

[73] Assignee: Smithkline Beecham Corporation, Philadelphia, Pa.

[21] Appl. No.: 445,245

[22] Filed: May 19, 1995

[30] Foreign Application Priority Data

Aug. 5, 1994 [GB] United Kingdom ............ 9415840

[51] Int. Cl.⁶ .................................................. A61M 31/00
[52] U.S. Cl. .................................. 604/279; 604/264
[58] Field of Search ........................... 604/36, 39, 181, 604/187, 257, 264, 275, 279, 280, 902

[56] References Cited

U.S. PATENT DOCUMENTS

| 205,353 | 6/1878 | Chamberlin . |
|---|---|---|
| D. 256,505 | 8/1980 | Strickman et al. . |
| D. 285,970 | 9/1986 | Pritchard . |
| D. 314,238 | 1/1991 | Gori . |
| D. 319,699 | 9/1991 | Dunning . |
| 3,228,396 | 1/1966 | Potts ........................... 128/232 |
| 3,474,788 | 10/1969 | Corbin et al. . |
| 3,512,526 | 5/1970 | Fielding . |
| 3,905,370 | 9/1975 | Lazdowski ..................... 128/232 |
| 3,968,509 | 7/1976 | Winkler et al. . |
| 3,968,797 | 7/1976 | Packer et al. . |
| 4,014,332 | 3/1977 | Sneider ......................... 128/227 |
| 4,068,662 | 1/1978 | Sneider . |
| 4,133,313 | 1/1979 | Sneider . |
| 4,167,186 | 9/1979 | Pick et al. . |
| 4,256,107 | 3/1981 | White . |
| 4,262,669 | 4/1981 | Sneider . |
| 4,309,995 | 1/1982 | Sacco . |
| 4,318,403 | 3/1982 | Sneider . |
| 4,351,336 | 9/1982 | Sneider . |
| 4,405,306 | 9/1983 | Pritchard et al. . |
| 4,519,794 | 5/1985 | Sneider . |
| 4,894,053 | 1/1990 | Reddick . |
| 4,906,239 | 3/1990 | Bruhl et al. . |
| 4,911,704 | 3/1990 | Dixon . |

FOREIGN PATENT DOCUMENTS

| 945860 | 4/1974 | Canada . |
|---|---|---|
| 1026635 | 2/1978 | Canada . |
| 1127927 | 7/1982 | Canada . |
| 1128394 | 7/1982 | Canada . |
| 1156892 | 11/1983 | Canada . |
| 1196541 | 11/1985 | Canada . |

*Primary Examiner*—Corrine M. McDermott
*Assistant Examiner*—Deborah B. Blyveis
*Attorney, Agent, or Firm*—Nora Stein-Fernandez; Janice E. Williams; Edward T. Lentz

[57] ABSTRACT

The invention relates to a novel douche nozzle suitable for vaginally administering a douche fluid.

2 Claims, 4 Drawing Sheets

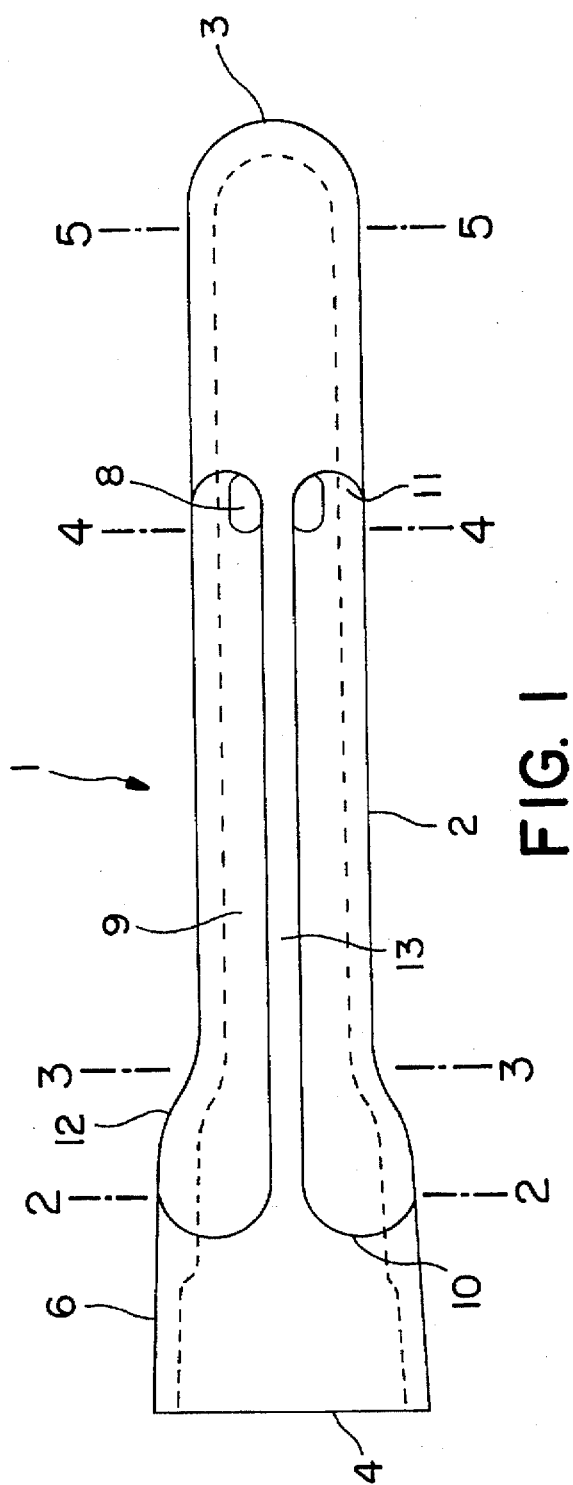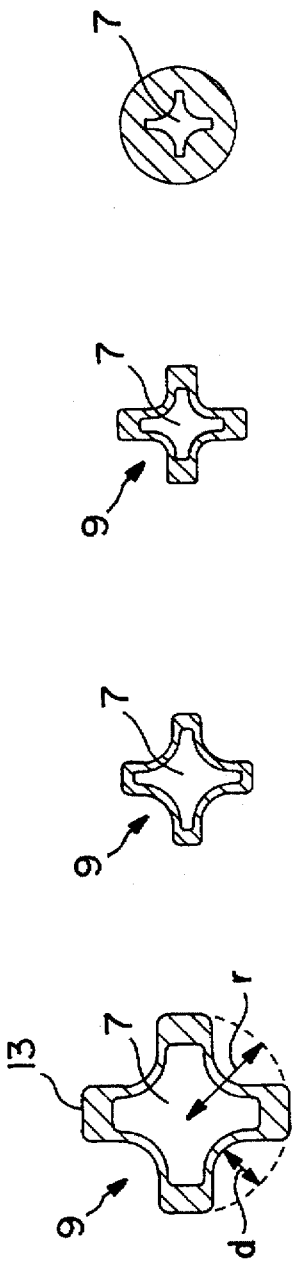

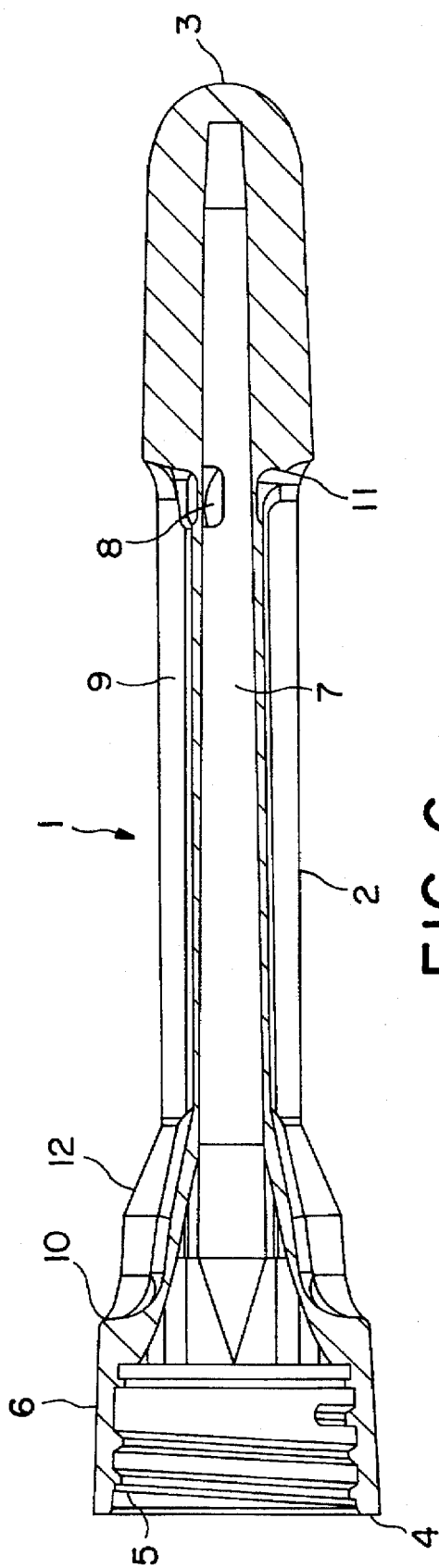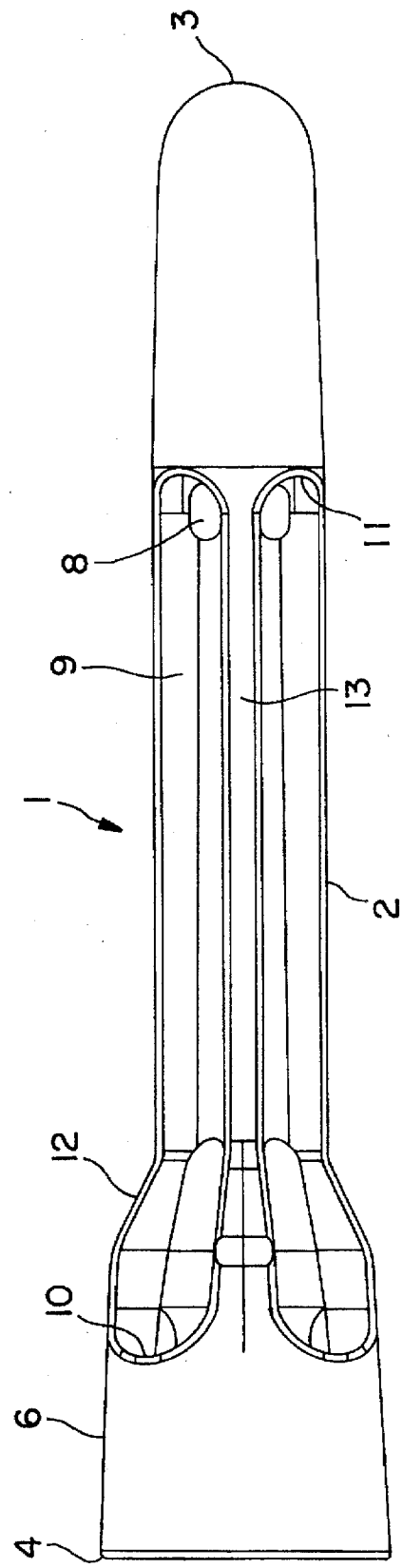

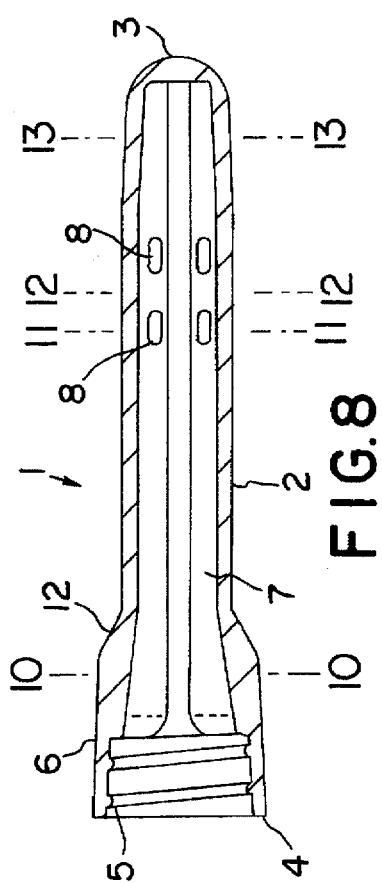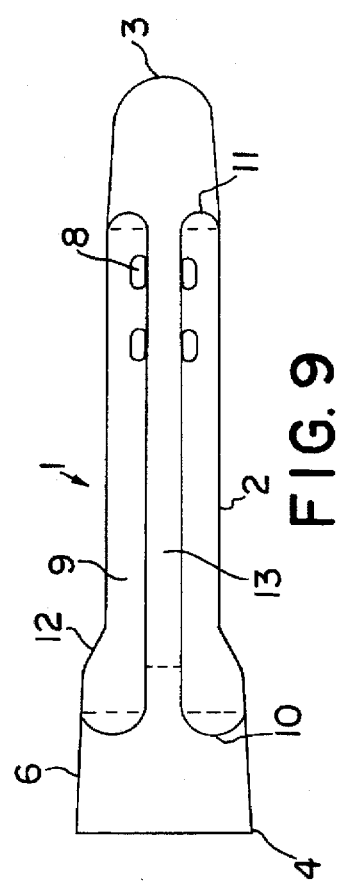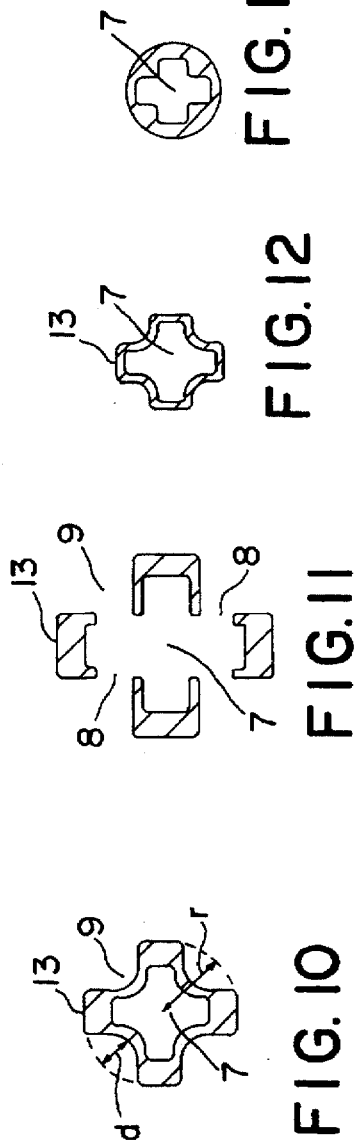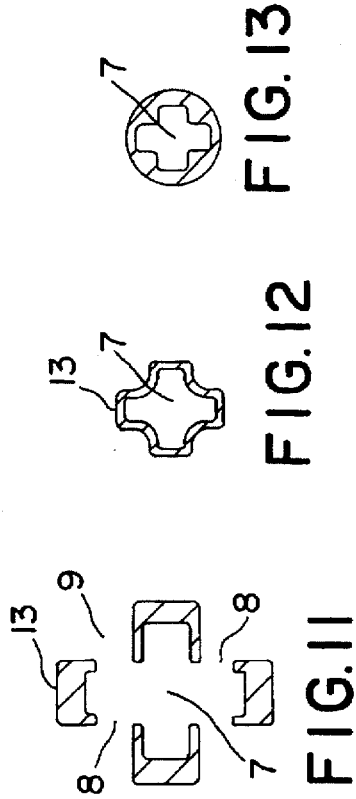

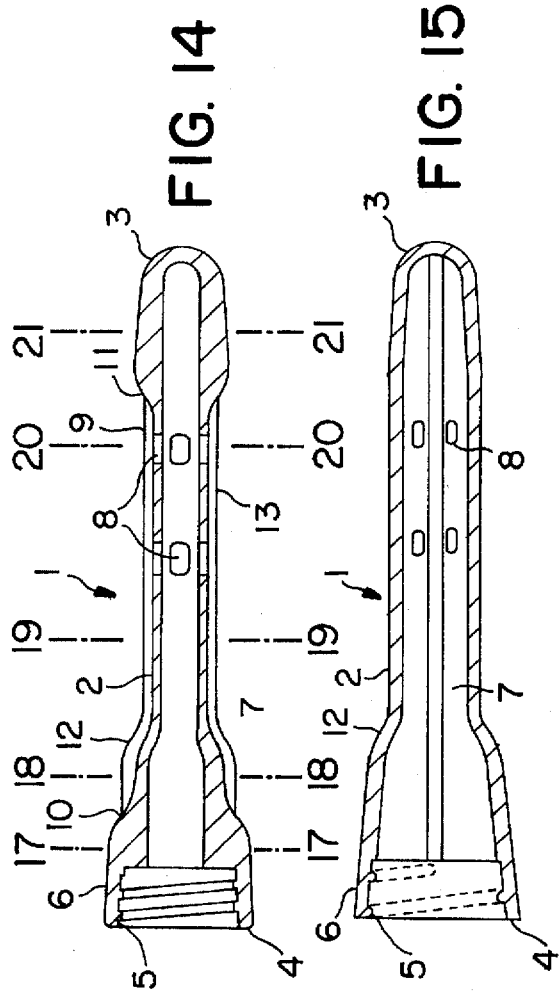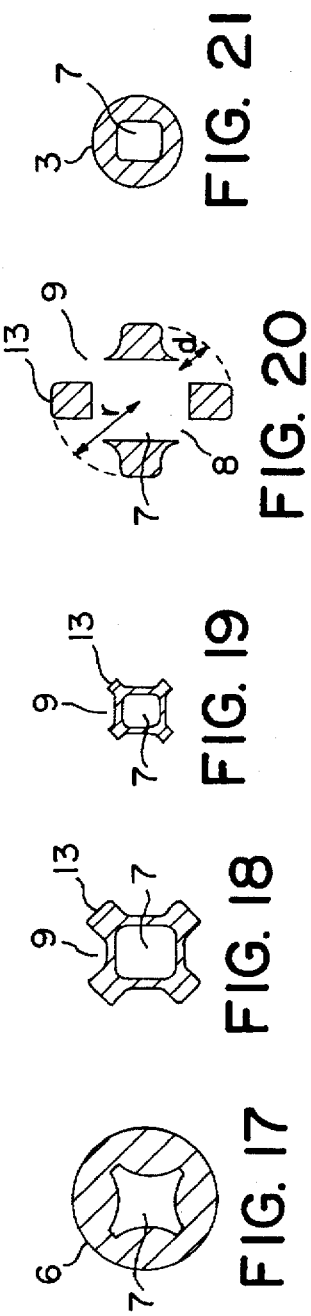

NOZZLE

This invention relates to a novel douche nozzle for use in the application of vaginal douche fluids.

Douche products are known and generally comprise a nozzle in the form of an elongate tubular body made of surfaced material, e.g smooth plastics material, with an opening in their proximal end for entry of a douche fluid, a generally longitudinal channel for the fluid, and one or more lateral apertures in the walls of the body for outward lateral flow of the fluid during use. Generally such nozzles are attachable at their proximal end to a squeeze bottle or other container for the fluid, e.g. by a screw thread or other type of convenient connector.

Douche nozzles are for example disclosed in U.S. Pat. Nos. 3,228,396, 3,474,788, 3,968,797, 4,068,662, 4,133,313, 4,167,186, 4,256,107, 4,309,995, 4,351,336, 4,405,306, 4,519,794 and 4,894,053.

Known douche nozzles suffer from the problem that the flow rate of fluid out through the apertures has not been optimised. A further problem is that transfer of fluid from the channel out through the apertures has not been optimised, which may cause development of pressure and poor performance in cleansing. Further it is desirable that the cervix is not irrigated by the douche fluid, and known douche nozzles do not achieve this requirement.

It is an object of this invention to provide an improved douche nozzle which to some extent at least overcomes the problems of known douche nozzles. Other objects and advantages of the invention will be apparent from the following description.

According to this invention, a douche nozzle suitable for dispensing a douche fluid comprises an elongate tubular body having an external surface and an internal substantially longitudinal channel terminating in an opening at the proximal end of the nozzle suitable for entry into the channel of a douche fluid, the channel being closed at its distanced, the body having one or more lateral apertures in its wall and communicating with the channel to enable fluid flowing along the channel to exit the body, a portion of the external surface of the body comprising one or more longitudinally extending recessed grooves having fluid diverters means, and characterised in that there is more resistance to fluid flow within the channel than there is resistance to fluid flow out through the apertures.

This characteristic feature of the invention contributes to the effect of ensuring that the pressure of the fluid drops as the fluid flows from the channel out through the aperture.

Preferably, the grooves are of such a size, shape, and orientation relative to the surface of the nozzle that in use there is less resistance to fluid flow along the grooves than there is resistance to fluid flow out through the apertures. This too contributes to the effect of ensuring that there is less fluid pressure as the fluid comes into contact with human tissue.

In a preferred embodiment of the invention the total area of the apertures in the surface of the body is greater than the cross sectional area of the longitudinal channel, at least between the opening at the proximal end and the apertures. This contributes to the avoidance of a squirting or jetting effect of the fluid out through the apertures. For example the ratio total area of the apertures: cross sectional area of the longitudinal channel may be in the range 1.0001:1 to 3:1, suitably between about 1.01:1 to 2:1.

These features of the invention assist in reducing the energy or pressure with which the fluid exits the nozzle and contacts the vaginal tissue, and therefore tends to alleviate the abovementioned problems associated with overpressurisation. In particular the constructional features of the nozzle of the invention are such that the resistance to fluid flow pressure is greatest inside the channel, before the fluid contacts the tissue, thus preventing any build up of pressure as the fluid flows out of the nozzle through the apertures and along the grooves and as it comes into contact with vaginal tissue during use. Thus an object achieved by the nozzle of the invention is a reduction of fluid flow pressure at the interface between the nozzle and the vaginal tissue. Resistance to fluid flow is greatest inside the nozzle, is less across the apertures and is reduced again in the grooves, thus ensuring that little pressure is developed as the fluid contacts the vaginal tissue.

In a preferred embodiment of the invention, the whole or part of the flow of fluid is diverted by the fluid diverter means from a lateral into a distal to proximal direction. This assists in reducing the tendency of the nozzle to cause irrigation of the cervix, and furthermore encourages the fluid to flow downwards during use, both assisting the douching action and contributing to the reduction in pressure as the fluid flows downwards along the grooves. Consequently it is preferred that the apertures are provided toward the distal end of the body, suitably in the half of the length of the body closest to the distal end. Suitably the apertures may be within 0.15 and 0.5, preferably within 0.2 and 0.4, of the distance from the distal end to the proximal end.

In addition to diverting the flow of fluid into a distal to proximal direction part of the fluid flow may be diverted into other directions, e.g. tangentially to the surface of the nozzle, or in a plane including the longitudinal axis of the nozzle.

In one embodiment of the invention, the flow of fluid is diverted by diverter means comprising the location of each aperture in the surface of the body, and/or by the location of each aperture adjacent to one or more diverter surfaces which are so profiled and/or positioned that at least part of the flow encounters the diverter surface and is thereby diverted. If the walls of the body are thick enough the diverter means may also comprise a profiling of the walls of the apertures.

In a preferred construction of the nozzle, each aperture is located in an area on the proximal side of a diverter surface. In such a construction, fluid flowing outwardly through the aperture has a natural tendency to spread sideways, and the encounter between the flow of fluid and the so-positioned diverter surface diverts the flow into a distal to proximal direction.

Diverter surfaces may also be included which divert the flow of fluid into the above-mentioned other directions.

The diverter surface may be in the form of a wall structure or surface adjacent to the aperture. The wall surface or structure may suitably be in the form of a generally laterally inclined planar or concave (relative to the aperture) surface formed in the surface of the body of the nozzle.

In a preferred embodiment of the invention, each aperture is located within and at the distal end, of a longitudinally extending recessed groove in the outer surface of the body, the extreme distal end of the groove comprising a diverter surface in the form of a wall surface. The location of apertures in such grooves further encourages the douche fluid to flow in a distal to proximal direction, i.e. within the grooves. In addition the location and size of the apertures within the grooves is an important factor in optimizing the fluid flow pressure, in combination with the channel size and cross sectional area. The apertures may suitably be at a distance proximally from the extreme distal end of the groove, typically being within about 0.3 of the length of the groove from the extreme distal end of the groove.

Apertures may also be located in other positions in the surface of the nozzle.

It has also been found that selection of a particular profile of such grooves is important in achieving optimum flow volume, pressure and direction, and moreover in reducing the tendency for musculature to close around the nozzle and thereby obstruct the flow of fluid. Therefore suitably the grooves do not extend for the entire length of the tubular body, but end about 0.2 to 0.35 of the distance from the distal end of the tubular body.

Suitably there are between two and ten recessed grooves in the external surface of the nozzle. A preferred form of the nozzle has four to eight grooves. More preferably the nozzle has between four to six grooves, typically four.

A suitable flow rate of douche fluid appears to be about 10 to 40 ml/sec, preferably 17 to 20 ml/sec. Therefore in a preferred embodiment of the invention the grooves are relatively deep, suitably having a depth of 0.3 to 0.8, preferably 0.4 to 0.8, of the radius or extrapolated radius of the body, particularly in the vicinity of the apertures, and preferably over a substantial part, e.g 0.75 or more of their length. Preferably where such grooves open out onto the outer surface of the body, the proportion of the circumferential perimeter of the body taken up by the open tops of the grooves may be 0.4 to 0.8, suitably 0.5 to 0.7, of the perimeter, particularly in the vicinity of the apertures. Typically the ratio depth : width of the grooves may be about 1:1.5–3.0, e.g around 1:2, particularly in the vicinity of the apertures.

Within the generality of the above many specific forms of the invention will be apparent to those skilled in the art. A preferred form of the nozzle has from four to twelve apertures, eight being preferred, located in the distal half of four respective grooves, the cross section through the nozzle over the region occupied by the grooves being generally cruciform, with the angles between the arms of the cross defining the grooves. In such a nozzle the apertures may be located in the surface of the body in a position such that the flow of fluid is diverted into a direction which is substantially parallel to a plane which includes the direction of two oppositely pointing arms of the cruciform section. The longitudinal channel within the body may suitably run along the axis where the arms of the cross meet. The longitudinal channel may have a cruciform cross sectional shape generally corresponding to the cross section of the body, or alternatively may have a generally square cross section, which may have rounded or truncated corners.

The dimensions of the nozzle may be similar to those of known douche nozzles, being determined primarily by anatomical considerations.

Suitably the opening at the proximal end of the nozzle suitable for entry into the channel of a douche fluid may form a connection for a container for a douche fluid. The container may be a conventional squeeze bottle, and the connection may comprise a conventional screw thread or snap or friction fit connection. The nozzle may therefore terminate in a base part comprising the connection. The part of body of the nozzle in the vicinity of the apertures may be of a narrower cross section than the base part, and the differing cross sections may be accommodated to each other by shoulders between the base part and the narrow part of the body. The grooves may be continued into the shoulders and optionally also into the base part, and this may assist the flow of the liquid during use.

The nozzle may be made of materials generally used in the manufacture of douche nozzles, such as smooth surfaced medically acceptable plastics materials such as polyethylene or polypropylene etc. Conventional moulding techniques, e.g. injection or blow moulding techniques can be used for forming the nozzle from such materials. Suitably such polymers may be treated with or include within their bulk medically acceptable lubricants, particularly lubricants which become slippery when they are wetted.

The invention will now be described by way of example only with reference to the accompanying drawings, which are intended to be illustrative of but not limiting the generality of the above disclosure.

FIG. 1 Shows a generalised side view of a nozzle of the invention.

FIGS. 2–5 Show cross sections of the nozzle of FIG. 1 respectively at longitudinal positions 2—2, 3—3, 4—4 and 5—5.

FIG. 6 Shows a more detailed part cutaway longitudinal sectional view of the nozzle of FIGS. 1–5.

FIG. 7 Shows a more detailed view of the nozzle of FIGS. 1 to 6.

FIG. 8 Shows a longitudinal sectional view through another nozzle of the invention.

FIG. 9 Shows a generalised side view of the nozzle of FIG. 8

FIGS. 10–13 Show cross sections of the nozzle of FIGS. 8 and 9 respectively at longitudinal positions 10—10, 11—11, 12—12 and 13—13.

FIG. 14 Shows a longitudinal section view through another nozzle of the invention.

FIG. 15 Shows a longitudinal section view through the nozzle of FIG. 14 perpendicular to FIG. 14.

FIG. 16 Shows a generalised side view of the nozzle of FIGS. 14 and 15.

FIGS. 17–21 Shows cross sections of the nozzle of FIGS. 14 and 15 respectively at longitudinal positions 17—17, 18—18, 19—19, 20—20 and 21—21.

Referring to FIGS. 1 to 7, a nozzle (1 generally) is shown. The nozzle (1) comprises a generally tubular body (2) having a smoothly rounded distal end (3) and a proximal end (4) having an opening with an internal screw thread fitting (5) within a base part (6) of the nozzle suitable for connecting the proximal end (4) to a squeeze bottle (not shown). Internally along the central longitudinal axis of the body (2) is a channel (7), running from the opening at the proximal end (4), to a point near the distal end (3). The internal outline of the channel (7) in FIG. 1 is shown by a dotted line.

In the body (2) of the nozzle are eight apertures (8), communicating with the channel (7) thereby permitting fluid flowing along the channel (7) from the proximal end (4) to the distal end (3) to exit the nozzle. The apertures (8) are located in the half of the length of the body (2) closest to the distal end (3), and are symmetrically disposed in two sets each of four apertures around the longitudinal axis of the body (2).

Each of the apertures (8) is located at the extreme distal end of a longitudinally extending recessed groove (9) in the outer surface of the body (2), the grooves (9) running longitudinally from this extreme distal end to a region (10) on the outer surface of the base part (6) of the body (2) near the proximal end (4). The extreme distal end of each groove (9) comprises a wall surface (11), in the form of a generally laterally inclined concave (relative to the aperture) surface formed in the surface of the body of the nozzle, immediately proximally adjacent to each aperture (8). The tubular body (2) of the nozzle has a narrower cross section than the base part (6), and the cross section of the body (2) and base part (6) are accommodated by shoulders (12). The grooves (9) extend into the shoulders (12).

The grooves (9) are defined by a generally cruciform cross section of the body (2) in the region of the body (2) occupied by the grooves (9) as shown in FIGS. 2 to 5 by the cross sections at the longitudinal points 2—2, 3—3, 4—4 and 5—5 respectively, the grooves (9) being defined by the angle between the arms (13) of the cruciform shape. The depth (d) of each groove (9) is around 0.5 of the extrapolated radius (r) of the body (2), and the proportion of the circumference of the body (2) over the region of the body (2) occupied by grooves (9) is about 0.6.

The cross sectional shape of the internal channel (7) conforms generally to the cross sectional shape of the cruciform-sectioned region of the body (2) occupied by the grooves (9).

In the vicinity of the apertures (8) the area of the apertures (8) is greater than the cross sectional area of the channel (7).

Referring to FIGS. 8 to 21, parts generally corresponding in construction and function to parts of the nozzle of FIGS. 1 to 7 are numbered correspondingly. Although the overall construction of the nozzle of FIGS. 8 to 21 is similar to that of FIGS. 1 to 7, the apertures (8) are not immediately adjacent to the extreme distal end (11) of the grooves (9) but are at a distance proximally therefrom, typically being within about 0.3 of the length of the groove (9) from the extreme distal end of the groove (9). The sections shown in FIGS. 11 and 20 are enlarged to show that the apertures are located in the surface of the body in a position such that the flow of fluid is diverted into a direction which is substantially parallel to a plane which includes the direction of two oppositely pointing arms (13) of the cruciform section. In the vicinity of the apertures (8), i.e. at the section points shown in FIGS. 11 and 20 the ratio total area of the apertures: cross sectional area of the longitudinal channel, being about 2:1 in FIGS. 8 to 13 and about 1.07:1 in FIGS. 14 to 21. As shown in FIGS. 10 and 20 the grooves (9) have a depth of about 0.4 of the extrapolated radius of the body (2) in the vicinity of the apertures (8). In the nozzle of FIGS. 14 to 21 the body 2 has an overall proximal to distal taper.

The dimensions of the nozzle shown in FIGS. 1 to 21 may be substantially the same as conventional nozzles, the overall length being about 12 cm, with a diameter at a median point, e.g the section B—B of FIG. 8 of about 12.5 mm, and an internal diameter at the screw fitting (5) of about 20 mm. Other dimensions of the nozzle illustrated may be determined empirically.

In use, a squeeze bottle (not shown) containing douche fluid is attached to the open proximal end (4) via the screw thread at (5). The body (2) is then inserted for use, and the douche fluid (not shown) is introduced into the channel by squeezing the bottle (not shown). Douche fluid exits through the apertures (7) and undergoes a pressure drop as the area of the apertures (8) is greater than the cross sectional area of the channel (7) in the vicinity of the apertures (8). The fluid also encounters the diverter surfaces (11) formed by the distal ends of the grooves (9) and as a result the flow is thereby diverted into a distal to proximal direction. The deep grooves (9) further encourage the fluid to flow in this direction, and the relative depth (d) of the grooves (9) prevents surrounding tissue from obstructing the flow of douche fluid in the distal to proximal direction. The continuation of the grooves (9) into the shoulder (12) and base region (6) assists drainage during use.

We claim:

1. A douche nozzle suitable for dispensing a douche fluid comprising an elongate tubular body having a proximal end and a distal end, and having an external surface and an internal substantially longitudinal channel terminating in an opening at the proximal end of the nozzle suitable for entry into the channel of a douche fluid, the channel being closed at its distal end, the body having one or more lateral apertures in its wall and communicating with the channel to enable fluid flowing along the channel to exit the body, a portion of the external surface of the body comprising one or more longitudinally extending recessed grooves having fluid diverter means, and characterised in that there is more resistance to fluid flow within the channel than there is resistance to fluid flow out through the apertures and wherein the total area of the apertures in the surface of the body is greater than the cross sectional area of the longitudinal channel, at least between the opening at the proximal end and the apertures.

2. A douche nozzle according to claim 1 wherein the grooves do not extend for the entire length of the tubular body, but end about 0.2 to 0.35 of the distance from the distal end of the tubular body.

* * * * *